US009138693B2

(12) United States Patent
Aouad

(10) Patent No.: US 9,138,693 B2
(45) Date of Patent: Sep. 22, 2015

(54) AUTOMATED HIGH PRECISION SOLUTION PREPARATION APPARATUS

(76) Inventor: Salah M. Aouad, Casablanca (MA)

( * ) Notice: Subject to any disclaimer, the term of this patent is extended or adjusted under 35 U.S.C. 154(b) by 807 days.

(21) Appl. No.: 13/426,261

(22) Filed: Mar. 21, 2012

(65) Prior Publication Data

US 2012/0241045 A1 Sep. 27, 2012

Related U.S. Application Data

(60) Provisional application No. 61/466,340, filed on Mar. 22, 2011.

(51) Int. Cl.
*B65B 1/04* (2006.01)
*B01F 1/00* (2006.01)
*B01F 13/10* (2006.01)
(Continued)

(52) U.S. Cl.
CPC ............ *B01F 1/0038* (2013.01); *B01F 13/1066* (2013.01); *B01F 15/00032* (2013.01); *B01F 15/00064* (2013.01); *B01F 15/0445* (2013.01); *G01G 19/24* (2013.01); *B01F 15/0441* (2013.01); *B01F 2015/0221* (2013.01); *B01F 2215/0014* (2013.01); *B01F 2215/0032* (2013.01); *B01F 2215/0037* (2013.01)

(58) Field of Classification Search
CPC ...... G01G 19/22; B01F 15/04; B01F 15/0441
USPC .............. 222/56; 141/9, 82, 83, 94, 100, 104, 141/105, 234, 236, 237; 177/122; 366/152.1, 134, 141, 142, 144, 177.1
See application file for complete search history.

(56) References Cited

U.S. PATENT DOCUMENTS 4,415,446 A 11/1983 Osborne ........................ 210/101
4,428,679 A * 1/1984 Fischer et al. ................. 366/141
(Continued)

FOREIGN PATENT DOCUMENTS

DE  10 2009 04051 A1  3/2011
JP       1 180229 A    7/1989
WO    WO 97/21528      6/1997

OTHER PUBLICATIONS

M. Legrand and P. Bolla, "A Fully Automatic Apparatus for Chemical Reactions on the Laboratory Scale", Journal of Automatic Chemistry, vol. 7, No. 1, pp. 31-37, (1985).
(Continued)

*Primary Examiner* — Jason K Niesz
(74) *Attorney, Agent, or Firm* — Winston & Strawn LLP

(57) ABSTRACT

The present invention relates to an automated solution preparation apparatus having containers for holding solid reagents, a dispensing mechanism for dispensing the reagents to a balance, a supply for providing liquid to rinse the reagents from the balance into a chamber where additional liquids can be added, and a manifold connected to the chamber for dispensing the solution into receptacles. The chamber can have probes for monitoring properties of the solution, and heating and cooling jackets for adjusting the solution temperature. The present invention also relates to a method for using the automated solution preparation apparatus to prepare solutions of different concentrations and properties by dispensing reagents from containers into a weighing zone, where each reagent is separately weighed and rinsed from the weighing zone into a chamber, diluting the reagents with additional liquid solvent to prepare the solution and discharging the solution from the chamber into receptacles.

24 Claims, 2 Drawing Sheets

(51) Int. Cl.
   *B01F 15/00* (2006.01)
   *G01G 19/24* (2006.01)
   *B01F 15/04* (2006.01)
   *B01F 15/02* (2006.01)

(56) References Cited

U.S. PATENT DOCUMENTS

| | | | |
|---|---|---|---|
| 4,469,146 A | 9/1984 | Campbell et al. | 141/9 |
| 4,476,999 A | 10/1984 | Bilbrey | 222/75 |
| 4,830,508 A | 5/1989 | Higuchi et al. | 366/152 |
| 4,964,185 A | 10/1990 | Lehn | 8/158 |
| 5,402,834 A | 4/1995 | Levin et al. | 141/83 |
| 5,607,651 A | 3/1997 | Thomas et al. | 422/266 |
| 5,632,960 A * | 5/1997 | Ferri et al. | 422/106 |
| 5,720,154 A | 2/1998 | Lasher et al. | 53/411 |
| 5,833,364 A | 11/1998 | Rushing et al. | 366/152.1 |
| 5,874,049 A | 2/1999 | Ferri, Jr. et al. | 422/106 |
| 6,007,236 A * | 12/1999 | Maguire | 366/141 |
| 6,061,608 A | 5/2000 | Moldavsky | 700/240 |
| 6,126,904 A | 10/2000 | Zuellig et al. | 422/130 |
| 6,224,252 B1 | 5/2001 | Munroe et al. | 366/132 |
| 6,357,906 B1 | 3/2002 | Baudoin et al. | 366/163.2 |
| 6,402,363 B1 | 6/2002 | Maguire | |
| 6,605,256 B1 | 8/2003 | Güller et al. | 422/99 |
| 6,764,212 B1 | 7/2004 | Nitta et al. | 366/114 |
| 6,827,478 B2 | 12/2004 | Becker et al. | 366/108 |
| 7,134,459 B2 | 11/2006 | Carlson et al. | 141/130 |
| 7,140,405 B2 | 11/2006 | Lewis et al. | 141/104 |
| 7,144,552 B1 | 12/2006 | Fukuizumi et al. | 422/62 |
| 7,222,753 B2 | 5/2007 | Hayduk | 222/145.5 |
| 7,361,309 B2 | 4/2008 | Vann et al. | 422/99 |
| 2003/0142580 A1* | 7/2003 | Maguire | 366/76.6 |
| 2003/0185094 A1* | 10/2003 | Packard | 366/141 |
| 2005/0047964 A1 | 3/2005 | Nishida et al. | 422/64 |

OTHER PUBLICATIONS

Article: "Accelerator SLT100/106/112 Synthesizer," Chemspeed Technologies®, 6 pages (2006).

Chata article, "Chem+Mix™ Automated Solution Preparation System Cost-Effective, Efficient, Convenient—It's all in the Mix", The Science of Lab Efficiency, www.Chatasolutions.com, 4 pages (2006).

International Search Report & Written Opinion PCT/MA2012/000003, dated Jul. 18, 2012.

* cited by examiner

AUTOMATED HIGH PRECISION SOLUTION PREPARATION APPARATUS

The present application claims the benefit of U.S. Provisional Application 61/466,340, filed Mar. 22, 2011, which is expressly incorporated herein by reference in its entirety for all purposes.

FIELD OF THE INVENTION

The invention relates to a computer automated apparatus used to automatically prepare chemical and biological solutions such as buffers, culture media, pharmaceutical preparations and other liquid mixtures that would be used for example in the pharmaceutical, chemical, biochemical or food industries, and a method of preparing such liquid mixtures using the disclosed apparatus.

BACKGROUND OF THE INVENTION

Many solutions are routinely used in laboratories and processing facilities for preparing sample batches and other liquid mixtures, as test solutions, or as stock solvents and mobile phases. Preparing such solutions requires much time to calculate the amount of reagents and dilutants, weigh the solid reagents, measure out the volumes of liquids for dilution, and combine these solution components in the correct amounts. These prepared solutions also require test measurement to confirm that they are the proper concentration or have the correct characteristics such as pH, conductivity or turbidity for their intended use. During the solution preparation and testing, the technician or scientist can be exposed to harmful chemicals and vapors that can damage their health. If a mistake is made during any of these steps, the preparer must start from the beginning, wasting the time and materials used for the solution preparation. Furthermore, the time spent making these solutions detracts from more valuable research and other duties personnel could be engaged in.

Different attempts have been made to automate this solution preparation process, such as U.S. Pat. No. 4,830,508 to Higuchi et al., but they have not fully automated a solution preparation process involving multiple solid reagents and liquid components in an accurate enough manner from multiple reagents to prepare solutions for a full range of laboratory and facilities uses. One such automated apparatus disclosed by Legrand and Bolla in "A fully automatic apparatus for chemical reactions on a laboratory scale", J. Automatic Chem., March 1985, is a custom laboratory device to be used when it is impractical to scale up a bench-top reaction. Such a custom device is used for running a chemical reaction, and is not intended to or capable of performing all the solution preparation tasks in the automated manner and at the scale of the present invention. Other devices have been devised to measure out liquids or premixed solutions to obtain specific concentrations or dilutions, but such devices still require the initial manual preparation of solutions that include solid reagents, which are then further diluted, such as that disclosed in U.S. Pat. No. 5,833,364 to Rushing et al., U.S. Pat. No. 5,402,834 to Levin et al., U.S. Pat. No. 4,415,446 to Osborn, and the Chem+Mix™ automated solution Preparation System marketed by CHATA. Device that measure out solids to form a solution are known in relation to the cleaning industries where concentrated wash solutions are prepared by adding detergents to a solvent, such as that disclosed in U.S. Pat. No. 4,964,185 to Lehn and U.S. Pat. No. 5,607,651 to Thomas et al., and in the paint and pigment industries where solid materials are metered out and blended with liquid components, such as in U.S. Pat. No. 6,827,478 to Becker et al. These devices, however, lack the features of the present invention that facilitate the accurate preparation of laboratory solutions. Similarly, other devices may measure out a specific amount of reagent or solution, but do not combine multiple components to form a solution or monitor and adjust the characteristics of the solution being prepared. Other device prepare multiple reaction solutions for screening reactions and products in chemical and biochemical laboratories, such as in U.S. Pat. No. 7,361,309 to Vann, U.S. Pat. No. 4,476,999 to Bilbery, and U.S. Patent Application Publication 2005/0047964 to Nishida et al. These devices dispense liquid reagents, but do not weigh out solid reagents to prepare a solution. The Accelerator™ SLT100/106/112 marketed by Chemspeed Technologies® prepares small amounts of reaction solutions from solids and liquids, and conducts reactions, but lacks the features necessary to produce larger amounts of laboratory solutions.

BRIEF SUMMARY OF THE INVENTION

Principles of the present invention relate to an automated apparatus that can automatically prepare solutions of a predetermined concentration from solid reagents and liquid components having predetermined chemical and physical characteristics with an accuracy that makes the prepared solution suitable for the majority of laboratory and facilities uses. According to such principles of the present invention it may be possible to reduce the amount of time routine solution preparation takes, and the amount of time technicians and scientists may be exposed to the solution, reagents and solvents. Some of the non-limiting embodiments of the invention may for example provide an apparatus that can deliver highly reproducible and reliable solutions by eliminating the variations in concentrations and properties resulting from the variability and human error present in the manual preparation of such solutions, and to thereby meet required quality control standards of laboratories and facilities. Another objective of the invention is to reduce waste of laboratory reagents due to mistakes made in the preparation of such solutions, and reduce the money and space required for laboratory glassware and other materials. Some embodiments of the invention can also maintain suitable and necessary records to be compliant with current good laboratory practices and good manufacturing practices.

In the case of non-limiting embodiments of the present invention, the term "predetermined" is to be interpreted as having been specifically selected by the user or set as a parameter in a computer file used to prepare the solution, and not changed or otherwise adjusted by the user once the automated preparation process has started.

In some embodiments, the user can choose to adjust the final solution parameters while the solution is still being prepared.

One or more of the embodiments of the present invention relate to a solution preparation apparatus comprising a plurality of containers for holding reagents, wherein the reagents held in the containers are solid reagents; a dispensing mechanism in flow communication and operatively associated with each container for selectively and sequentially dispensing an amount of one or more reagents from the one or more containers, wherein the dispensing mechanism comprises a plurality of conduits connected to the egress end of the respective containers, and a plurality of valves connected to and in flow communication with the conduits where a single valve is connected to each of the plurality of conduits; a balance for sequentially receiving dispensed reagent(s) and weighing each received reagent, wherein the balance has one or more balance plate(s), which are suspended below the egress ends of the conduits of the dispensing mechanism and suitably dimensioned for receiving and weighing a plurality of sequentially dispensed reagents at the same time without loss of any reagent from the balance plate; a supply for providing liquid for removing the reagents from the balance and for forming a concentrated solution, wherein the liquid is preferably deionized water, and further wherein the liquid is provided to the weighing zone through suitably sized piping and at a pressure that produces a suitable spray to wash the reagents from the balance plates; a chamber for receiving the concentrated solution and additional liquids for preparing a liquid mixture or solution of a predetermined volume, wherein the chamber has a chamber wall that can be insulated for maintaining the chamber at a consistent temperature and also has heating and cooling jackets within the chamber wall for adjusting the temperature of the chamber and solution; probes associated with the chamber for monitoring chemical and physical properties of the solution; and a solution distributor in fluid communication with the chamber for dispensing the solution into receptacles. The apparatus can further comprise one or more liquid reagent dispensers that can provide one or more liquid reagents to the chamber, wherein the liquid reagents can be acids, bases, buffers or detergents or solutions of acids, bases, buffers or detergents for adjusting the properties of the solution being prepared.

Embodiments of the apparatus can further comprise a volume detector in operative association with the chamber for determining the volume of solution within the chamber, wherein the volume detector comprises an infrared light source, floating disc and a detector in operative association with the light source and floating disc, that measures the liquid level in the chamber by detecting when the floating disc blocks the infrared beam at a particular level. The level of the floating disc correlates to a particular volume of solution in the chamber.

In another embodiment, the apparatus can further comprise a sterilizer tank for eliminating biological organisms and contaminants, wherein the sterilization tank is located in between and in liquid communication with the chamber and the manifold, and filters for removing particulates from the solution before discharging the solution into one or more receptacles. The apparatus can further comprise filters for removing particulates from the solution before dispensing the solution into receptacles, wherein the filters are located in and in fluid communication with the solution distributor. The filters can be located at the ingress or egress opening(s) of the sterilization tank or at the one or more ingresses or egresses of the manifold, such that the filters are located within the flow path of the solution to remove particulates when the solution passes therethrough. The solution can be sterilized and filtered in either order, but in either case before being discharged to the receptacles. The receptacle are preferably plastic or glass bottles, but may also be cartons, cans, bags, totes, or other containers known in the art for storing, dispensing and transporting solutions.

Embodiments of the apparatus can further comprise a processor for controlling the dispensing, weighing, mixing, adjusting and discharging processes. The processor can also receive signals from probes, sensors and detectors conveying information about solution properties, process such signals, and send control signals to valves, pumps, heating or cooling devices, stirrers or other actuators to adjust the concentration or properties of the solution. The processor can monitor the weights or volumes of the solid and liquid reagents, bulk solution and final dispensed solutions through weight or volume sensors, and record such information to properly document the preparation of the solution in compliance with current good laboratory and manufacturing practices (cGLP, cGMP). The processor can also store programs for operating the apparatus, files with instructions for automated preparation of predetermined solutions, and data obtained from the probes, sensors and detectors regarding the preparation of a solution, in the associated memory, where the memory can be both static and dynamic. The memory can be RAM, a hard drive, a CD or floppy drive, a memory card or any other type of transient and non-transient memory known in the art. The processor, memory, interface cards, and peripherals can be a dedicated controller or a stand-alone computer such as a personal computer (PC).

Embodiments of the apparatus can further comprises a plurality of separate compartments, wherein each separate compartment houses a different subset of the apparatus components, and wherein the compartments can be sealed from the outside atmosphere, and the atmosphere inside the chamber may be temperature and/or humidity controlled. Access to each chamber can be by one or more access port(s) having door(s) or airlocks that can form an airtight seal between the compartments and the outside environment. Each compartment is also separated and seal from the other compartments so that each may maintain a different controlled environment. Each of the compartments may also have a separate exhaust for removing gasses, vapors, dust or other airborne contaminants and maintaining a safe and proper atmosphere.

In a preferred embodiment of a solution preparation apparatus, the apparatus comprises a plurality of containers for holding canisters; a plurality of conduits, wherein a single conduit is connected to and in flow communication with an egress end of one of the plurality of containers; one or more canisters containing solid reagents placed within a respective container, and connected to the egress end of the container so as to form an airtight seal between the canister and the conduit; a dispensing mechanism comprising a plurality of valves connected to and in flow communication with the plurality of conduits; and a dispenser block supporting the valves and conduits, such that the dispensing mechanism is operatively associated with each container that selectively and sequentially dispenses an amount of one or more reagents; a balance comprising one or more balance plate(s) that sequentially receives the dispensed reagent(s) from an egress end of each of the plurality of conduits, and weighs each received reagent; a supply that provides liquid to the balance for removing the reagents from the balance and forms a concentrated solution; a chamber that receives the solution of solid reagents and liquid from the balance; a volume setting system that determines the volume of solution within the chamber; a pump that delivers liquid to the chamber until the volume setting system indicates the solution has reached a predetermined amount; and a valve that releases the solution from the solution into a manifold that dispenses the released solution into one or more receptacles. The apparatus may further comprise a sterilization tank, which is suitable for destroying biological contaminants, between the chamber and manifold, connected to the egress end of the chamber below the chamber valve and having an outlet connected to the dispensing manifold.

Embodiments of the present invention also relate to a method of preparing solutions which comprises providing a plurality of reagents; selectively and sequentially dispensing reagent(s) from reagent containers into a weighing zone, wherein the amounts of the one or more reagents dispensed into the weighing zone are each individually controlled by a computer actuated valve; receiving the reagents selectively and sequentially in the weighing zone, wherein each dispensed reagent is separately weighed; providing a liquid solvent; spraying the liquid solvent into the weighing zone for rinsing the dispensed reagents from the weighing zone; rinsing the one or more dispensed reagents from the weighing zone into a chamber with the spray of liquid solvent and forming a concentrated solution; receiving the concentrated solution from the weighing zone in the chamber; providing a liquid solvent to the chamber to dilute the concentrated solution of solvent and dispensed reagents; diluting the concentrated solution of solvent and dispensed reagents from the weighing zone with additional liquid solvent to prepare a solution of predetermined concentration; discharging the solution of predetermined concentration from the chamber to one or more solution receptacles.

The method can further comprising providing one or more liquid reagents; injecting one or more of the liquid reagents into the concentrated solution of solvent and dispensed reagents received in the chamber, wherein the liquid reagents adjust one or more properties of the concentrated solution including pH, conductivity, surface tension, or suspended particles, to produce a final solution having a predetermined concentration and physical and chemical properties, wherein the physical and chemical properties of the present invention can be determined by suitable probes transmitting signals to a processor.

The method can also further comprise detecting signals from the balance, calculating the amount of additional reagents to dispense to the balance based on the signals received by a processor, dispensing additional reagent to the balance until the processor determines the correct amount of reagent has been dispensed to prepare a solution of the predetermined concentration, and sending a control signal to an actuator stopping the dispensing of reagent to the balance.

The embodiments of the method can also further comprise detecting signals from the probes, sensors or detectors associated with the chamber, calculating the amount of additional liquid reagents to dispense to the chamber based on the signals received by a processor, dispensing additional liquid reagent to the chamber to adjust one or more chemical or physical properties of the solution until the processor determines the correct amount of liquid reagent has been dispensed to prepare a solution of the predetermined chemical or physical properties, and sending a control signal to an actuator stopping the addition of liquid reagent to the chamber.

The embodiments of the method may also comprise recording the values of the amounts of reagents and solvents dispensed, the concentration and physical and chemical properties as measured by probes during the preparation and once completed, and storing the recorded information in accordance with cGLP and cGMP requirements.

The principles of the invention also relate to a non-transitory computer readable medium that can be implemented that stores machine readable instructions for performing a process or method such as the examples of processes, methods, and steps described herein, or variations thereof as would be understood by a person of ordinary skill in the art.

Embodiments of the invention also relate to a non-transitory computer-readable medium that stores computer-readable instructions for execution by a processing system, the computer readable instructions for preparing solutions comprising; instructions to activate a valve for selectively and sequentially dispense reagent(s) from reagent containers into a weighing zone; instructions to separately weigh each of the selectively and sequentially dispense reagent(s); instructions to activate a pump for providing one or more liquid reagents for rinsing the one or more dispensed reagents from the weighing zone into a chamber; instructions to activate a pump for providing a liquid solvent to the chamber to dilute the concentrated solution; and instructions to open a valve for discharging the solution of predetermined concentration from the chamber to one or more solution receptacles.

The embodiments can also comprise a processor that can read the instructions from a computer readable medium and cause the computer-controlled components to perform the steps of the different embodiments of the invention and to carry out any one of the methods disclosed herein. The electronic device can also comprise the electronics necessary for communication with the computer controlled components, for example the valves, probes, pumps, stirrers, and other components, as would be known to those of skill in the automation arts.

BRIEF DESCRIPTION OF THE DRAWINGS

The above features and other advantages of the invention will become better understood by reference to the following detailed description of preferred embodiments and the accompanying drawings wherein.

DETAILED DESCRIPTION OF THE INVENTION

It should be understood that the figures and following descriptions are of exemplary embodiments of the present invention and are not intended to limit the scope of the invention in any manner. Other variations and embodiments of the present invention would be apparent to persons of ordinary skill in the art without departing from the spirit and principles of the invention, and all such variations and embodiments are intended to be included within the scope of the disclosure for the present invention and protected by the accompanying claims.

Figure 1:
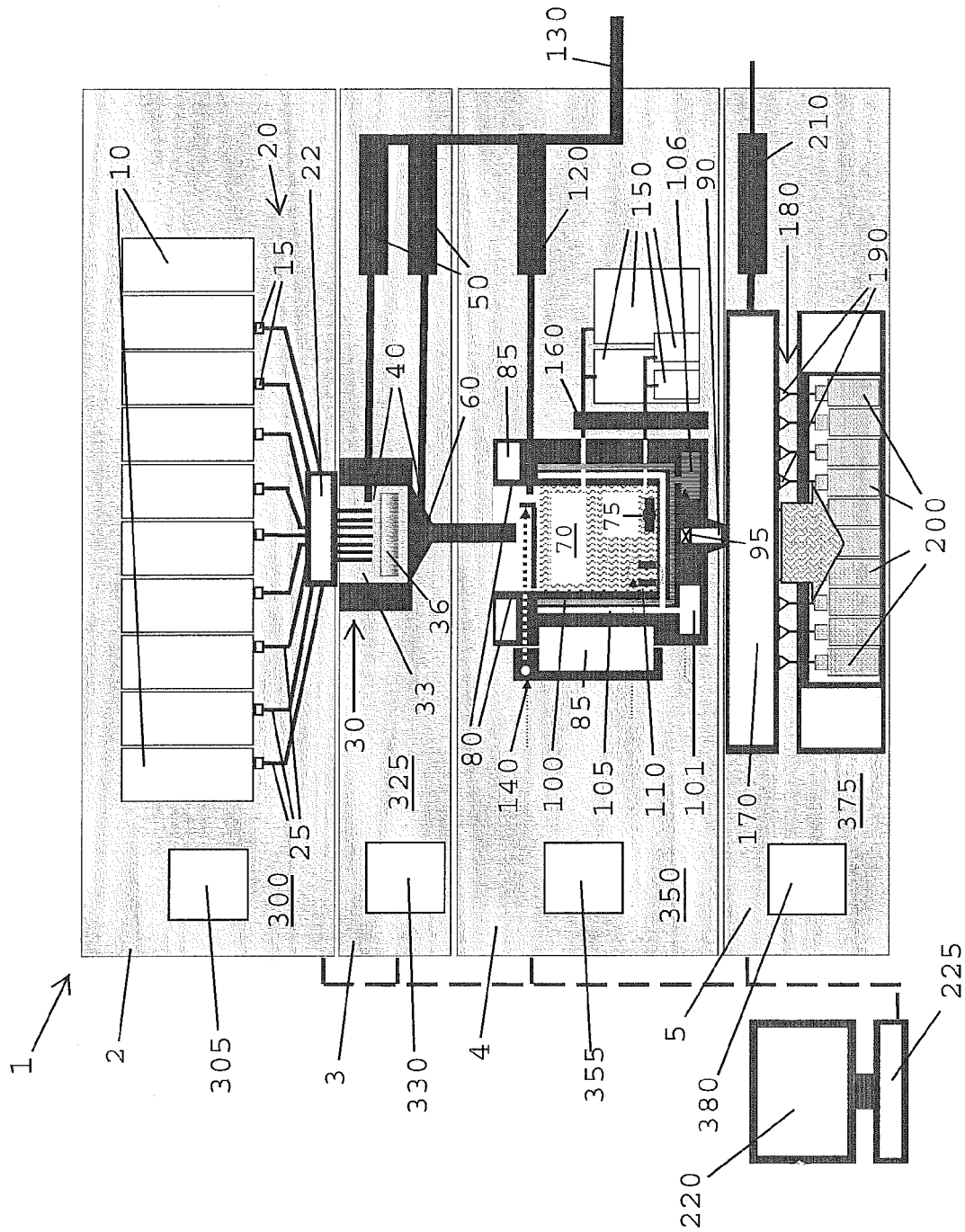
FIG. 1 is a front view of an automated solution preparation apparatus illustrating a preferred embodiment of the present invention.

In an example of a preferred embodiment, an apparatus 1 having four sections 2, 3, 4, 5, can automatically prepare solutions of predetermined concentrations from solid reagents and liquid components having predetermined chemical and physical characteristics with an accuracy that makes the prepared solution suitable for the majority of laboratory and facilities uses. As shown in FIG. 1, an embodiment of the apparatus has a plurality of containers 10 for holding reagents, a dispensing mechanism 20 for selectively and sequentially dispensing one or more reagents, a balance 30 for weighing each received reagent, one or more spray nozzle(s) 40 connected to and in fluid communication with pumps 50 for pumping solvent to the spray nozzles for rinsing reagents from the balance with bursts or sprays of the solution solvent, a collector 60 that collects the concentrated solution of reagent(s) and solvent from the sprays and directs the concentrated solution to the chamber 70 for adjustment of the solution properties and dilution to a final volume and concentration, wherein the chamber 70 has stirrers 75, walls 80 that can have insulation 85, a funnel shaped bottom 88 with a drain 90, a heating jacket or coil 100, and/or a cooling jacket or coil 105. The heating and cooling jackets or coils 100, 105 can have reservoirs 101, 106 that help to maintain a stable temperature and flow of heating or cooling fluid. The heated or cooled fluid is circulated through the respective reservoir, jacket and/or coils.

The chamber 70 can have probes, sensors or detectors 110 for measuring various properties of the solution as it is being prepared. A pump 120 in fluid communication with the chamber 70 and a solvent supply 130 can pump solvent into the chamber 70 from the solvent supply 130 to increase the volume of solvent in the chamber 70 to a final level detected by a volume setting system 140, wherein the volume setting system can have a transmitter 142, a floating disc 145 and a detector 147 in operative association. Liquid reagents in reagent reservoirs 150 can be added to the chamber 70 by pumps or injectors 160 in fluid communication with the liquid reagent reservoirs 150 and chamber 70.

The prepared solution having a predetermined concentration exits the chamber through the drain 90 when valve 95 is opened and optionally flows to a sterilization tank 170 for killing undesirable biological contaminants, and then to a solution distributor 180. If there is no sterilization tank 170, the final prepared solution having a predetermined concentration and physical and chemical properties can flow through the chamber drain 90 to the solution distributor 180, wherein the solution distributor can be a manifold for dispensing to the solution receptacles 200. Such a manifold may comprise a series of interconnected pipes or conduits that evenly and uniformly conveys the solution to the final receptacles. The solution may also be filtered through filters 190 located either at the egress(es) of the sterilization tank 170 or at the ingress(es), egress(es) or within the solution distributor 180. In some embodiments, the manifold can be separate pipes or conduits connected to the egress ends of the filters in order to maintain any differences in the solutions due to the size or type of filter used. In other embodiments, the solution can be drawn into the sterilization tank or through the filters using a vacuum 210, or forced through the filters under pressure (not shown).

Various embodiments of the apparatus are controlled by a processor 220 with associated memory 225 such as a personal computer. The computer would have sufficient transient RAM memory, non-transient storage memory, processing power, and hardware, such as interface cards to run the associated control software, interface with and operate the automated components of the apparatus, such as the various pumps, valves, sensors, and detectors, and record the values from the sensors, probes and detectors.

In some embodiments, the reagent containers 10 and dispensing mechanism 20 can be within a first compartment 300 that isolates the containers 10 and dispensing mechanism 20 of the first section 2 from the outside atmosphere and the other sections 3, 4, 5, of the apparatus 1 without interrupting the reagent flow communication between the dispenser and the balance 30. The balance 30, spray nozzle(s) 40, and collector 60, can likewise be within a second compartment 325, which isolates section 3 from the outside atmosphere and the other sections 2, 4, 5, without interrupting reagent flow or liquid communication between the dispensing mechanism 20 or chamber 70. The chamber 70, drain 90, probes 110, volume setting system 140, liquid reagent reservoirs 150, and injector(s) 160, are within a third compartment 350, that isolates the third section 4, from the outside atmosphere and the other sections 2, 3, 5, without interrupting liquid communication between the collector 60 and sterilization tank 170 or solution distributor 180. The sterilization tank 170, solution distributor 180, filters 185, and receptacles 200 are within a forth compartment 375, that isolates the forth section 5, from the outside atmosphere and the other sections 2, 3, 4, without interrupting liquid communication between the chamber 70 and drain 90, and the sterilization tank 170 or solution distributor 180. The compartments 300, 325, 350 and 375 may have individual access ports 305, 330, 355, 380 that allow separate access to sections 2, 3, 4, 5, respectively for such things as clearing clogs, making repairs or replacement of components.

In embodiments of the present invention, multiple reagent containers 10 are situated in the first compartment 300 at the top of the apparatus 1 above the other components. These containers 10 are sized and shaped to hold specially designed canisters 11 that preferably contain solid reagents. The containers can preferably be cylindrical, but can also be hexagonal, square, rectangular or any other shape that can be arrayed in a regular pattern while allowing access for changing their contents. The term solid is meant to include all solid particles having a sufficiently small size and either regular or irregular shapes, such as powders, crystals, pellets, grains, flakes, filings, shavings, dust, etc. This plurality of containers is arranged in a regular manner such that they could be operatively associated with the dispensing mechanism. The canisters 11 are also sized to hold sufficient amounts of reagents for preparing a plurality of solutions before having to be replaced, and shaped to fit within the containers 10 in a manner that provides easy insertion and removal, such as a slip fit. The canisters can also preferably be cylindrical, but can also be hexagonal, square, rectangular or any other shape that can preferably be arrayed in a regular space-saving pattern. The canisters 11 in a preferred embodiment have a spout at a bottom end that is closed with a removable cap, and an opening at a top end opposite the first end that has a removable covering. The canister 11 can be inserted into the container 10 by first removing the cap from the spout at the first end and placing the canister bottom end first into the container. The spout at the bottom end of a canister 11 is suitably configured and dimensioned to join with the ingress end of the dispensing mechanism 20, and preferably forms a seal between the canister and the dispensing mechanism 20. In a preferred embodiment, after the cap is unscrewed from the spout, the spout is screwed into the ingress end of a conduit 25. A seal is also preferably formed between the canister 11 and the container 10, such as by a gasket or bevel (not shown). Each of the seals preferably prevents the entry of contaminants, gasses and moisture into the canisters and conduits. The removable covering can then be removed from the top end of the canister to prevent a vacuum from forming in the canisters so the reagent flows smoothly. There can be a mesh or screen or other semi-permeable membrane secured over the top opening to protect the reagent from contaminants, gasses or moisture after the covering is removed. The caps and coverings are preferably screw caps but may also be snap lids, foil pull-seals, or any other type of removable closure known to those skilled in the art.

Figure 2:
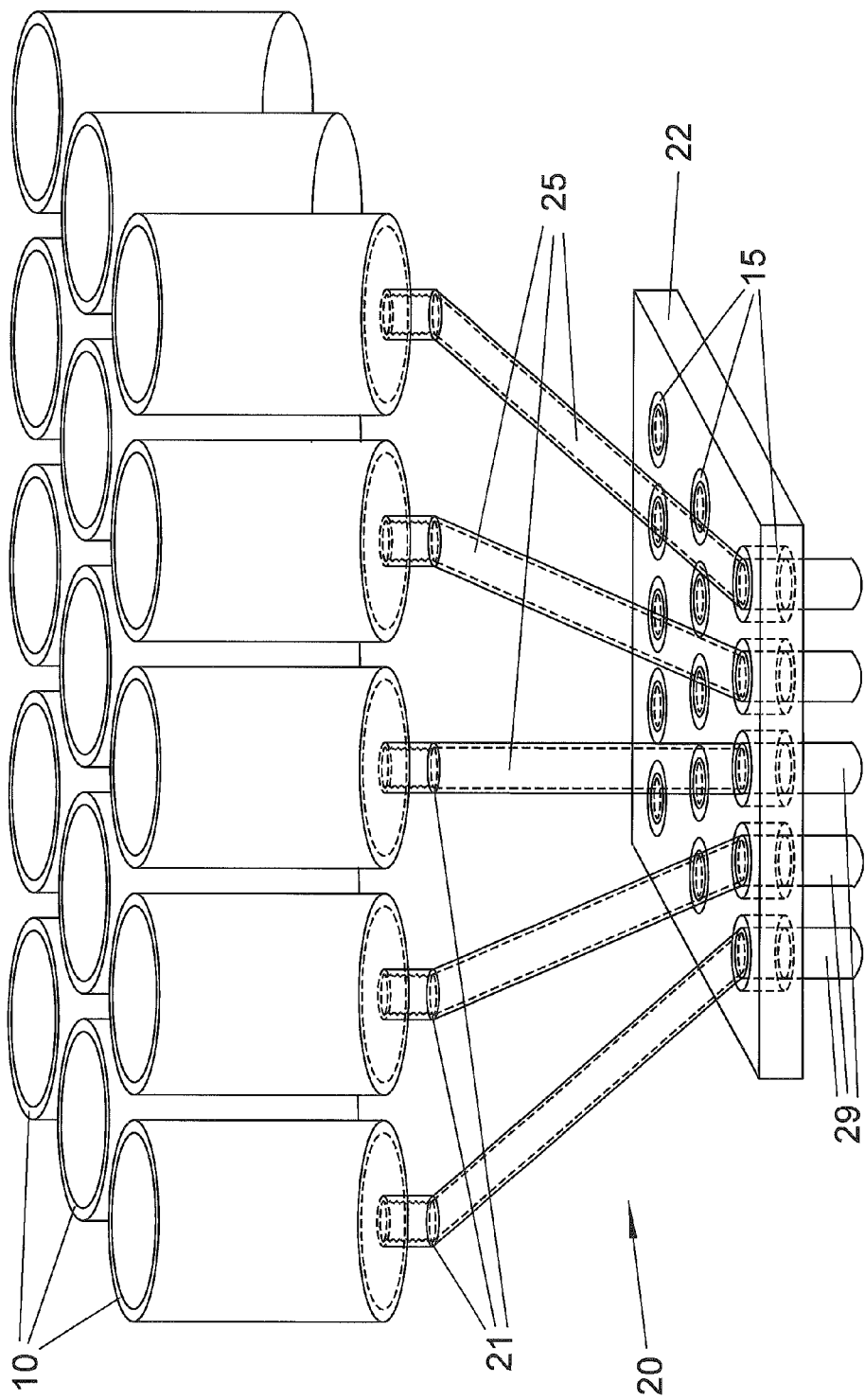
FIG. 2 is a detailed view of a preferred embodiment of the containers and dispensing mechanism.

In some embodiments, the dispensing mechanism 20 comprises an array of conduits 25, an array of valves 15, and a dispenser block 22, such as flexible tubing or more rigid piping that are in flow communication with the array of containers 10 holding the canisters 11 of the solid reagents. The ingress ends 21 of the array of conduits 25 are arranged in the same pattern as the array of canisters and containers, such that the conduits match up and become associated with the canisters to allow solid reagent to flow from any or all of the multiple containers to a location above the weighing zone 33 of a balance 30. The conduits can be attached to the egress end of the containers with a disengagable connector such as a threaded coupling or it may be permanently attached using a permanent adhesive, brazing, soldering or welding depending upon the materials being used for the respective components. Flow of the solid reagents is controlled through the use of valves 15 activated by and in operative association with dispensing mechanism 20, wherein each conduit has its own independently controlled valve that prevents the solid reagent from a particular container from being dispensed to the weighing zone 33 of the balance 30. The valves 15 may be located at the ingress end of the conduit, or more preferably at the egress end or at some position between the two ends of the conduits within the dispensing mechanism 20. In the best mode, as illustrated in FIG. 2, the valves 15 are held in a regular array within the dispenser block 22, and each valve is connected to and in flow communication with the egress end 29 of a conduit. Each valve is therefore associated with and in flow communication with a specific container and canisters through the respective conduit. The dispenser block can be a solid block holding or incorporating the valves, or it may also be a series of walls separating the array of valves from each other to prevent cross contamination of reagents, and covers to close the openings in the block. FIG. 2 depicts such an arrangement of valves located in a solid dispenser block and in flow communication with the conduits and containers (where some features and duplicated components are not drawn to maintain the clarity of the drawing). The dispenser block and valves also act as a seal between compartment 300 and compartment 325 when the valves or dispenser block openings are closed. In the preferred embodiment, the valves and dispenser block are placed as close to the balance as possible without interfering with the dispensing or weighing operations to provide the most accurate method of weighing the reagents. Placing the dispenser block and valves as close to the balance plate as possible reduces the amount of material present in the gap between the two components that has not yet been weighed. In an embodiment where the valve are located by the containers, along the conduit, or otherwise away from the dispenser block, the egress ends of the conduits are preferably connected and in flow communication with the openings in the dispenser block 22, and the dispenser block has doors, slides or other covers that can close the openings in the dispenser block to preferably prevent the entry of reagents, solvents, gasses, vapors, moisture or other contaminants into the conduits and compartment 300 from the weighing area 33 of the balance 30, or from compartment 325.

When a valve 15 is opened, solid reagents may flow through the conduits 25 by gravity feed, or the particle flow may be augmented or further controlled by known feed assist mechanisms and methods such as augers, vibratory mechanisms and feeders, entrainment by venturi systems, compressed air-assist, blowers, other types of positive pressure or vacuum, etc. In a preferred embodiment, one or more feed assist mechanisms may also be present to facilitate the flow of any reagents from the containers and canisters through the conduits and valves to the weighing zone 33 of the balance. The rate at which a solid reagent is released from a container or a conduit is preferably controlled by restricting the time and/or extent to which the valve is opened. The term "extent" is to be interpreted as the available cross-sectional area of the valve opening across which there is a flux of material independent of the design of the valve mechanism, and restricting the extent should be interpreted to mean changing the cross-sectional area in a manner that reduces the flux of material through the valve due to a smaller opening and/or a reduction in flow velocity of material. For example, the valve opening may be contracted or restricted to reduce the rate of flow when the balance registers that a predetermined amount has been dispensed to more slowly approach the final weight, and thereby achieve more accurate control of the total amount dispensed. In another embodiment, the valve opening could also remain open until the balance registers for example 99% of the final weight, and then be fully closed with the expectation that the amount of reagent dispensed in the brief interval before the valve completely closes will still be sufficiently accurate. The actual percentage of weight dispensed before closing the valve would be determined based on the flow properties of the solid, such that a known or calculatable amount of solid powder would exit the valve before it was fully closed. This amount or weight of material can be determined and calibrated by the processor quickly opening and closing the valve for a specific reagent a predetermined extent multiple times and measuring the actual amount dispensed to the balance with each such cycle of the valve. The actual dispensed amounts can then be compared and averaged to determine the weight at which a specific valve for that particular reagent should be closed to accurately achieve the needed final weight. This method avoids the user having to prepare new calibration standards for each solution or perform other measurements to calibrate the apparatus.

The dispensing mechanism 20 can selectively dispense each reagent, as specifically required to prepare a solution, in a sequential manner to the weighing zone 33 of the balance. This results in a dispensing cycle where the dispenser opens the valve to the first required reagent thereby allowing the solid to flow to the weighing zone, and when the correct weight of this first reagent is reached, the valve stops the flow of that reagent, and opens the valve to the next required reagent. The dispenser 20 repeats this cycle until all the required solid reagents for preparing the specified solution have been sequentially dispensed to the weighing zone in the correct amounts. Once a reagent is dispensed and properly weighed, it does not matter if subsequently dispensed reagents intermix with the prior ones because the amount of each dispensed reagent is determined by the difference in weight at the beginning and end of a dispensing cycle. The sequence of dispensing each reagent, however, may be chosen to facilitate the flow of each reagent by dispensing sticky, forming or very fine materials in a preferred order. This cycle can be repeated as many times as is required to dispense all the reagents needed to prepare a specific solution.

In embodiments of the invention, the balance(s) 30 receive(s) the dispensed reagents in a weighing zone 33. The weighing zone can include one or more balance plates 36, where a single balance plate would have a size sufficient to hold the total amount of reagents that would be used to prepare any of the required solutions. The balance plate 36 is appropriately sized and shaped to be capable of retaining the total amount of the one or more reagents received in the weighing zone 33, and obtain an accurate final weight by avoiding any reagent falling off the balance plate. In some embodiments, a number of balance plates of differing sizes from ½ liter to 100 liters can be provided for the user's selection based upon the amounts of materials to be accurately weighed, and exchanged as needed before solution preparation. Two or more balance plates may also be placed within the weighing zone for improved accuracy and precision in weighing greatly different amounts of reagents with a diverter or orientatable nozzle (not shown) to direct each reagent to the appropriately sized balance plate. Each balance plate would have a size appropriate for holding and accurately weighing a portion of the total amount of reagents to be used to prepare a required solution. Having two or more balance plates within the weighing zone also avoids the need to exchange balance plates during a solution preparation.

Preferably each of the one or more balance(s) is a high precision suspended balance, where the balance plate is connected to a precision weighing mechanism or load cell outside the weighing zone and shielded from the solvent spray and solid reagent dust. The balance plate(s) can be suspended below the egress ends of the conduits comprising the dispensing mechanism. Some embodiments contemplated for the present invention would utilize two balances with one having a large balance plate dedicated to weighing large weights, and the second balance having a small balance plate dedicated to weighing smaller weights, where the precision and accuracy of the smaller balance could be greater than the precision and accuracy of the larger balance.

Embodiments of a balance plate preferably have vertical or inwardly slanted walls that would act to retain dispensed materials on the balance plate's base. The base plate can be a single plate, or preferably it may be divided into two or more sections that act as doors, which open slowly to prevent lighter or fluffier materials from dispersing or being suspended in the air when being transferred to the chamber 70. The sections or doors of the base plate are preferably attached to the walls of the balance plate. The base plate or plurality of opening sections can have on or more pneumatic or hydraulic pistons or actuators to open or close the plate section(s).

Each of the one or more balance plates' walls and base(s) can be sprayed with a liquid solvent from spray nozzles 40 to aid in transferring the weighed solid reagents into the collector funnel 60 and chamber 70.

The balance can measure the weight of each reagent as it is sequentially dispensed to the weighing zone 33. The balance 30 determines the amount of the solid reagent received on the balance plate 36 by registering the initial weight of the plate and any previously received reagents before the next reagent is dispensed, and the accumulated weight after the reagent is dispensed. The balance 30 detects the difference between the initial weight and accumulated weight to determine when the final weight is obtained. The processor can receive the weights from the balance sensors, and calculate when the final weight is obtained. The weighing proceeds one reagent at a time in a sequential manner until all necessary reagents have been dispensed. The weight of each sequentially dispensed reagent is recorded for the preparation of the solution in accordance with cGLP and cGMP requirements.

The each of the one or more balances 30 has sufficient precision and accuracy to weigh out an amount of reagents within a tolerance acceptable for the lab or production facility within a prescribed range for the balance's size. Preferably each balance is capable of accurately weighing to within 0.001 gram, but the demands of the particular use may require a more accurate balance or allow the use of one with less accuracy, also depending upon the total amount of material to be weighed by the particular balance. A person of ordinary skill in the art will be aware of the necessary accuracy and precision for their own particular uses.

Reagents dispensed to the balance(s) 30 can be washed after weighing from the weighing zone 33 and balance plate(s) 36 with bursts or sprays from spray nozzles 40 of the liquid being used as the solvent component of the prepared solution. The liquid is provided to the weighing zone through suitably sized piping and at a pressure that produces a suitable spray to wash the reagents from the balance plates. These bursts or sprays of solvent reach all surfaces of the weighing zone 33 and wash all of the dispensed solid reagents from the balance plate 36 into a collector 60. The solvent is preferably forced from the solvent source 130 through suitable piping to the spray nozzles 40 by pumps 50 that are in fluid communication with the spray nozzles 40 and solvent source 130, and can generate bursts or sprays of suitable pressure to rinse all the reagents from the weighing zone without requiring a quantity of solvent greater than would be needed to prepare a solution of a particular final concentration. The collector 60 can be a funnel or other suitably shaped feature that directs the concentrated solution into the chamber 70 while avoiding the trapping or adhering of any residue reagent powders or solution. This first solvent spray prevents any of the dispensed reagents from remaining in the weighing zone 33, and ensures that the total amount of weighed reagents is included in the chamber. The collector is preferably washed by a second solvent spray that prevents any of the concentrated solution washed from the weighing zone from remaining in the collector. The second solvent spray rinses the bottom of the balance plate and the reagent and solution from the first spray from the collector 60 to the chamber 70. The amount of solvent used to wash the weighing zone 33, balance plate 36 and collector 60 is less than the total volume that will be used to prepare the final solution of the predetermined concentration. The combination of solid reagents and solvent at this stage therefore forms a concentrated solution that will be diluted to a final volume and concentration in the chamber 70. The collector 60 can be a funnel that directs the concentrated solution of solid reagents and solvent into the chamber 70. The first and second solvent sprays ensure all of the reagents weighed out in the balance 30 are quantitatively transferred to the chamber 70 for final dilution. This quantitative transfer of material helps to achieve the concentration of the final solution within the expected accuracy and precision.

The solvent 130 would preferably be water, and more preferably high purity deionized water, but may also be a saline solution, alcohol, acetone, hexane, or some other aqueous-based or organic liquid. The particular choice will depend on the type of final solution the user may typically be preparing. Examples of possible uses include liquid chromatography mobile phases, buffer solutions, biological or biochemical media, electrophoresis gels, colloids, or reaction solutions.

In some embodiments of the present invention, the liquid reagents are stored in the liquid reagent reservoirs 150, which can be acids, bases, surfactants, detergents or other polymers, as well as organic liquids like dyes and those listed above. The acids could be mineral acids such as phosphoric, sulfuric, nitric or hydrochloric acids, or organic acids such as acetic, oxalic, malic, tartaric or citric depending upon the type of solution to be prepared and the type of buffer system being used. Such solutions can be prepared by the apparatus and then used as a solvent or liquid reagent. The user of the apparatus 1 would select the materials that would be appropriate for the particular solutions that the user would be preparing without limitation to the materials mentioned. One or more pump(s) 120 and/or injector(s) 160 feed the solvents and liquid reagents into the chamber. The pump(s) 120 feed the solvent(s) into the chamber until the necessary volume is reached, at which time the pump(s) are shut off. Liquid reagents are transferred by injector(s) or pump(s) 160 from the reagent reservoirs 150 into the chamber 70 until a particular property of the solution, such as pH, is reached, and then the injector or pump stops.

The concentrated solution is received in a chamber 70. The chamber can have walls 80 made of material suitable to hold the solutions being prepared without causing contamination or being damaged by the solutions. The chamber walls 80 can be insulated 85 and further surrounded with heating and/or cooling jackets or coils 100, 105 to control the temperature of any solution being prepared. The heating and cooling jackets or coils can have reservoirs 101, 106 to help maintain a stable temperature and constant flow of heating or cooling fluid. The heated or cooled fluid is circulated through the respective reservoir and jacket to adjust and/or maintain the chamber and solution at a suitable and stable temperature. Preferably the chamber, heating and cooling jackets are stationary and does not need to be raised or lowered to receive solution, or be heated/cooled. The solution is received from the collector 60 directly into the chamber 70. An egress from the chamber 70 in the form of a drain 90 having a valve or a plug 95 that prevents the flow of the solution from the chamber is preferably positioned at the bottom of the chamber in a manner that would allow all of the solution to leave without pooling or leaving more than a minimum of residue. The chamber preferably has a funnel shape that directs all of the solution out through the drain 90. The drain is in liquid communication with a solution distributor 180 that can be a liquid manifold and/or a tank with one or more egresses that directs the final prepared solution to empty receptacles 200 for easier distribution, storage, and later use. The distributor can be configured and dimensioned to allow filling of receptacles from ½ liter to 10 liters, or more preferably from 1 to 4 liters in size, although larger or smaller receptacles could be filled without deviating from the scope or intent of the present invention. The receptacles 200 may be for example, plastic or glass bottles, cartons, cans, bags, or totes depending on the use and storage requirements of the user.

In various embodiments, the chamber can have devices such as probes, stirrers, detectors or analyzers 110 for monitoring the chemical and physical properties of the solution being prepared. Such devices could preferably be electrodes for conductivity measurements, temperature probes, pH probes, solubility probes, turbidity detectors or nephelometers, specific gravity probes, optical rotation detectors, and UV, IR and NIR spectrometers. The probes, sensors and detectors monitor physical properties of the solution such as temperature, amount of suspended particles, viscosity and density and send signals to a processor for adjusting the properties to a predetermined value by heating, cooling, or adding additional liquid reagents. Other probes, sensors and detectors can also monitor chemical properties such as pH, solubility, salinity, conductivity and chemical composition, such as by infrared or near infrared in situ monitors, and send signals to a processor for adjusting such values to a predetermined level by adding additional liquid reagents. A camera associated with the chamber 70 can also be used to observe the solution during preparation to detect undissolved solids or other visual abnormalities in the solution.

In embodiments of the invention, a volume setting system 140 can be in operative association with the chamber 70, and determines the volume of solvent added to the solution by detecting the level of solution in the chamber. The volume setting system 140 preferably uses an infra-red transmitter that produces a linear light beam, a floating disc and a receiver that detects the location of the beam. The linear light beam travels across the chamber 70 at a predetermined height corresponding to the needed final volume of solution to the receiver. The receiver preferably can be an array of infra-red detectors that positioned vertically on the side of the chamber 70 opposite the transmitter. The receiver detects the light beam from the transmitter until the floating disc interrupts the light beam, when the needed volume of solution is reached. The solvent pump(s) 120 feed solvent into the chamber until the floating disc interrupts the infrared beam preventing the beam from reaching the detector. The solvent feed is stopped when the volume setting system 140 indicates the correct volume is reached. Once the light beam is interrupted, the pumps and any active stirrers are stopped to allow the surface level of the solution to stabilize. If the solution level decreases after the surface has stabilized, the floating disc ceases to interrupt the light beam and additional solvent will be pumped into the chamber 70 until the final volume is reached. Once an accurate final volume is reached, the stirrers and probe will be activated to ensure a homogenous solution with the required properties has been prepared. If the solution is at the predetermined volume, but the sensors detect the solution properties are outside of the predetermined range(s), the processor can send a warning and request for corrective action to the user. Although the infrared arrangement is the preferred embodiment, other detection methods such as ultrasonic level sensors, floats, capacitance detectors, pressure sensors or other means known to those in the art may also be used to determine the solvent level in the chamber.

In other embodiments, the solution manifold 180 may optionally be connected to and in fluid communication with a sterilization tank 170, which is located between and in liquid communication with the chamber drain 90 and the solution manifold 180 for sterilization of the final prepared solution and filtration before distribution to the final receptacles. The tank can also have one or more egresses that are in fluid communication with the receptacles through suitable tubing or piping. Filters 190 can be fitted in the one or more sterilization tank egresses to remove unwanted particulates of a particular size or larger before the solution enters the receptacles 200. Filters 190 can also be fitted within each fluid communication path to provide greater filtration surfaces and avoid clogging of such filters, or to allow differentiation in filtration size to prepare solutions or suspensions, such as colloids, of varying grades or properties. The filters may preferably have between 0.22 um and 0.45 um pores for example, or any other pore size as known to those of ordinary skill in the art that meet the solution preparation requirements.

The sterilizer 170 can be a heated tank that can raise the temperature of the final solution to a temperature needed to kill biological organisms or destroy biological contaminants, or it could have devices such a UV lighting, ozone generators, or other sterilization devices known to those of ordinary skill in the art for accomplishing such sterilization. The solution can be drawn into the sterilizer tank 170 and through the manifold 180 and filters 190 by a vacuum 210. The vacuum is preferably in gaseous communication with the manifold, so as to suction the solution through the tank and any intervening conduits forming the manifold. The vacuum in a preferred embodiment is preferably connected to the apparatus in such a manner so as to suction the solution through any filters, however the solution may also pass through the filters under gravity. In one embodiment, the filter can be located at the egress end of the chamber drain 90, and the vacuum can be in gaseous communication with the sterilization tank. In another embodiment, the filters 190 can be located at each of a plurality of connecting openings between the sterilization tank 170 and the manifold 180, and the vacuum is in gaseous communication with the manifold at a location downstream of the filters 190. Suitable baffling and screens known in the art should be used to prevent drawing the solution into the vacuum or entrainment of the solution in the vacuum flow.

In some embodiments, the apparatus is controlled by a processor 220 that has associated memory 225 that can store programs and data. The processor can read instructions from a computer readable medium and cause the computer-controlled components to perform the steps of the different embodiments of the invention and to carry out any one of the methods disclosed herein. The processor is connected to peripheral input and output device such as keyboards, mice, displays and printers, as well as other device known to those in the art of computers and processors. The computer(s) can also comprise hardware, software and firmware necessary to store, process, and communicate with a variety of other devices, as would be known in the art. The operations of the apparatus including the dispensing, weighing, washing, diluting, mixing, and discharging are all controlled by the processor. The processor can be connected to components of the apparatus such as the balance as well as probes, sensors and detectors to receive information for processing, and transmit instruction signals to components or actuators such as the reagent dispenser valves, augers, vibratory mechanisms, pumps, solvent sprays, liquid reagent dispensers, heaters, coolers and other devices. The components, detectors and sensors can provide feedback to the controller, so that it can control other components and actuators based upon the signals and record the solution properties. This feedback allows the processor to monitor and control the preparation of the solution and correct for any discrepancies based upon such signals. The processor receives signals from the balance 30, and probes, sensors and detectors 110 conveying information about the solution properties, processes such signals, and sends control signals to valves, pumps, heating or cooling devices, stirrers or other actuators to adjust the concentration or properties of the solution or advance the preparation of the solution to a subsequent step. The controller 220 can adjust the amounts of materials added to the solution to produce a final product with the requested and necessary properties. The processor can be a computer work station as know to those of ordinary skill in the art, or an application specific controller having all the basic components of a computer but also with specialized components for connecting to and interacting with all the apparatus components, sensors and actuators.

The apparatus 1 can further comprise a processor 220 for controlling the dispensing, weighing, and mixing processes. The processor 220 can also store an operating system and programs for operating the apparatus 1, files with instructions for automated preparation of predetermined solutions, including solution preparation instruction previously entered by a user, and data obtained from the probes, sensors and detectors 110 regarding the preparation of a solution, in the associated memory 225, where the memory 225 can be both static and dynamic.

The memory in association with the processor can store programming instructions and data files that contain selections of reagents and solution volumes for preparing particular final solutions. These instructions can be activated, and/or data files read to prepare predefined solutions. Once activated the programming will control the apparatus automatically to prepare a chosen solution. For example, the processor 220 and memory 225 would control the sequence of the reagents dispensed to the weighing zone 33, open and close the individual valves 15 to control the weights of each reagent dispensed based upon the signal from the balance 30, spray the solvent into the weighing zone 33 to wash the reagents into the chamber 70 once all reagents were weighed, increase the volume of solvent in the chamber 70 by tuning on the pump 120 for the solvent, turn on stirrers 75 to mix the solution as it is being prepared, and stop the pump 120 once the correct volume and concentration are reached. The memory 225 can also store signals from the balance 30 and sensors 110 to monitor the changes in the solution for quality control and documentation purposes to meet good laboratory and manufacturing requirements. Such documentation can then be printed out for quality control and compliance, laboratory or manufacturing records.

In a preferred embodiment, a user can recall a file storing instructions and parameters for preparing a solution and loading it to the computer, where the computer 220 activates the dispensing mechanism 20 to dispense predetermined amounts of one or more reagents to the balance 30 based on instruction stored in a file in the memory 225. The balance 30 sends signals to the computer 220, which continuously monitors the increase in weight for each sequentially dispensed reagent. The computer 220 sends a signal to the dispensing mechanism 20 to close the valve 15 when the measured weight of the reagent on the balance plate 36 reaches 99% of the predetermined amount indicated in the instructions. The next selected reagent is then sequentially dispensed to the balance 30 and weighed in the same manner. This is repeated until all the required reagents have been dispensed and weighed to the balance plate 36. The computer activates the pump 50 to spray solvent into the weighing zone 33 to rinse the dispensed reagent(s) from the balance plate 36 into the chamber 70. The computer 220 then monitors the solvent level and solution properties in the chamber. The computer will turn on the stirrers 75 to ensure the solution has a uniform concentration and consistency, or the heating 100 and cooling 105 jackets. When the volume setting system 140 send a signal to the computer 220 that the predetermined volume of solution has been reached, the computer 220 turns off the solvent pump 120, opens the drain 95, and turns on the vacuum 210 to draw the solution out of the chamber 70, through the manifold 180 and discharges it into the awaiting receptacles 200.

Once a solution is prepared and the preparation cycle is finished, the computer can turn on the pumps 50, 120 to wash any remaining reagents or solution from the apparatus. The solvent flushes all the apparatus components and is discarded though a waste line that can be attached to an egress of the manifold or suctioned out using the vacuum. Large volumes of solvent and extended durations of spraying can be used to ensure all reagent and solution residue is flushed from the apparatus. Hot air produced by devices known in the art can then be forced through the apparatus to dry any remaining solvent and vent the vapors. In the preferred embodiment, hot air guns flush the weighing zone compartment 325 with hot air to evaporate any remaining solvent from the balance(s) 30 and weighing zone walls.

The apparatus preferable can produce between ½ and 100 liters, and more preferably 1 and 10 liters of solution at one time.

The components of the apparatus can be made from stainless steel, aluminum, non-ferrous alloys, Teflon®, high density poly ethylene (HDPE), or any other material understood by those of ordinary skill in the art for use in particular applications that may depend on the solution acidity or alkalinity, salinity, temperature, or other chemical or physical properties, as well as the ability to prevent contamination and be properly cleaned between solution preparations.

In some embodiments, the apparatus 1 preferably comprises four sections 2, 3, 4, 5, in flow communication with each other that can be housed within four separate compartments 300, 325, 350, 375, wherein the compartments are airtight. The compartments may each also have access ports to allow access to the apparatus components that can maintain an airtight seal when any access port or opening 310 is properly closed and/or sealed preferably with an airtight door 320. Access to each separate compartment would be by opening the air-tight door(s) or airlock(s) 320. By making the compartments airtight when sealed, the temperature, humidity, pressure, and atmospheric gasses can be controlled for prevention of contamination and maintenance of suitable preparation conditions. The temperature, humidity, pressure, and atmospheric gasses can be adjusted with suitable devices known in the art for such purposes, such as compressed gas cylinders, heaters, air conditioners, dehumidifiers, etc. This may be particularly important in the second section 3, where the reagents are weighed and initially mixed with the solvent. The compartments can also be used to contain and exhaust undesirable or dangerous fumes by having the compartments in flow association with venting conduits that remove gasses or fumes or duct from the separate compartments by vacuum or positive pressure, and evacuate them to a fume hood, remediation system or the outside.

Embodiments of the present invention also relate to a method of preparing solutions using an automated high precision solution preparation apparatus comprises providing a plurality of reagents, wherein the reagents are solids that may be in a canister, loading the solid reagents or solid reagent canisters into the solid reagent containers, dispensing solid reagents from the containers, wherein the solid reagents are dispensed by automatically activating a dispensing mechanism such as valves to selectively and sequentially dispense the solid reagent, automatically dispensing the solid reagent selectively and sequentially to a balance, weighing each selectively and sequentially dispensed solid reagent by measuring the difference between the detected weight before the solid reagent is dispensed and the weight detected by the balance after the selected solid reagent is dispensed. Washing or rinsing the solid reagent from the balance into a collector, and receiving the solution directed by the collector in a chamber. Prefilling the chamber with a portion less than the total volume of solvent needed. Adding the one or more solid reagents to the prefilled chamber. Diluting the received solution to a predetermined concentration by increasing the volume of solvent making up the solution, and adding amounts of additional liquid reagents to affect other solution properties. Adjusting the chemical and/or physical properties, such as the pH, of the solution by adding sufficient amounts of liquid reagents to obtain the required solution property. Adding sufficient solvent to bring the volume of solution to the final predetermined amount. Dispensing the solution to a plurality of receptacles.

An embodiment of the method can further comprise stirring the solution in the chamber to thoroughly mix the reagents and solvents, detecting physical and/or chemical properties of the solution with probes as it is being prepared, discharging the solution from the chamber through a drain by vacuum; filtering the solution to remove suspended particles before discharging it to a plurality of receptacles, where the solution is pulled through the filter(s) by vacuum, sterilizing the solution before discharging the final prepared solution to a plurality of receptacles, wherein sterilizing can be accomplished by suitably heating the solution, exposing the solution to UV radiation or ozone to kill any biological organisms or destroy biological contaminants.

In another embodiment, the method can further comprise adjusting the temperature of the chamber and solution by circulating a temperature control medium such as heated or cooled fluids through the heating and/or cooling jackets. The method can also further comprise detecting signals from the balance, calculating the amount of additional reagents to dispense to the balance based on the signals received by a processor, dispensing additional reagent to the balance until the processor determines the correct amount of reagent has been dispensed to prepare a solution of the predetermined concentration, and sending a control signal to an actuator stopping the dispensing of reagent to the balance.

In another embodiment, the method can also further comprise detecting signals from the probes, sensors or detectors associated with the chamber, calculating the amount of additional liquid reagents to dispense to the chamber based on the signals received by a processor, dispensing additional liquid reagent to the chamber to adjust one or more chemical or physical properties of the solution until the processor determines the correct amount of liquid reagent has been dispensed to prepare a solution of the predetermined chemical or physical properties, and sending a control signal to an actuator stopping the addition of liquid reagent to the chamber.

The method can also comprise loading software into a computer for operating the apparatus and controlling the activation of the individual components of the apparatus, wherein the computer has a processor that can run the software and control the components of the apparatus by sending and receiving signals to the sensors and actuators. The computer can initiate preparation of a predefined solution by loading a data file into the computer memory or receiving input from a used through an input, such as a keyboard, and activating the valves and feed assist mechanisms to sequentially and selectively dispense solid reagents from each of the one or more solid reagent containers onto a balance plate in the weighing zone, and receiving a measurement signal from the balance indicating an accurate real-time weight of reagent dispensed to the balance plate. The actual final weighed amount of each dispensed reagent can be recorded and stored in memory by the computer. The computer can then close the valve feeding the selected reagent at the correct predetermined weight communicated from the load cell or sensor of the balance. Once the correct weight of each reagent has been dispensed to the balance, the computer can activate the pumps for the solvents in fluid communication with the spray nozzle(s) within the weighing zone. The computer may determine the maximum amount of solvent to be used to was the reagents from the balance plates without over-diluting the solution.

Once the concentrated solution is washed into the chamber, the computer can activate the solvent pump and increase the amount of the solution to a final volume and concentration. The computer may also receive signals from the sensors in the chamber indicating the various chemical and physical properties of the solution, and activate pumps for dispensing other liquid reagents or reactants to adjust these chemical and physical properties based upon the feed-back from the sensors. The computer can also activate stirrers within the chamber to make sure the solid reagents become dissolved and the properties being measured are uniform throughout the prepared solution. Each or the sensor reading may be recorder by the computer and software and suitable reports generated to allow the apparatus to comply with cGLP and cGMP requirements. Once a solution having the corrected concentration and properties is prepared, as determined by the volume measuring system and sensors, the computer can open the valve at the bottom of the chamber to dispense the solution to the solution manifold, optional sterilization tank, and final receptacles. The computer may also activate a vacuum or pressure system to assist in conveying the final solution to the receptacles. The computer software may then initiate a cleaning cycle to assure that all of the components and compartments are rinsed, clean and dry to prevent contamination of any successive solution to be prepared. Each of the other components of the system may be connected to the computer with suitable sensors and actuators to permit additional computer control and feed-back as is known in the art of equipment automation.

In one or more exemplary embodiments, the functions described may be implemented in hardware, software, firmware, or any combination thereof. If implemented in software, the functions may be stored on or transmitted over as one or more instructions or code on a computer-readable medium such as non-transitory computer readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

A person of ordinary skill in the art will recognize other modifications and variations including changes in the arrangement or sequence of the inventive features and operations described above. All such modifications and variations are intended to be within the scope and spirit of the present invention, as set forth in the following claims, and not limited by the particular embodiments or specific examples detailed above which are only intended to illustrate some of the variations and preferred embodiments of the present invention.

What is claimed is:

1. A solution preparation apparatus, the apparatus comprising:
   a plurality of containers for holding reagents;
   a dispensing mechanism in flow communication and operatively associated with each container that selectively and sequentially dispenses an amount of one or more reagents;
   a balance that sequentially receives the dispensed reagent(s) and weighs in a cumulative way each received reagent;
   a mixing chamber that receives the concentrated solution and additional liquids to adjust and prepare a liquid mixture of a predetermined concentration, wherein the mixing chamber has a chamber wall; and
   a supply that provides liquid to the balance for removing the reagents from the balance and forms a concentrated solution.

2. The apparatus of claim 1, which further comprises:
   a solution distributor in fluid communication with the chamber that conveys the discharged solution into receptacles.

3. The apparatus of claim 2, which further comprises:
   a processor for controlling the dispensing, weighing, mixing, adjusting and discharging processes.

4. The apparatus of claim 1, which further comprises:
   one or more liquid reagent dispensers that can provide one or more liquid reagents to the chamber.

5. The apparatus of claim 4, wherein the liquid reagents can be acids, bases, buffers or detergents or solutions of acids, bases, buffers or detergents.

6. The apparatus of claim 1, which further comprises:
   a volume detector in operative association with the chamber for determining the volume of solution within the chamber.

7. The apparatus of claim 6, wherein the volume detector comprises:
   an infrared light source;
   a floating disc; and
   a detector in operative association with the light source and floating disc, that measures the liquid level in the chamber.

8. The apparatus of claim 1, wherein chamber wall is insulated for maintaining the chamber at a consistent temperature.

9. The apparatus of claim 8, which further comprises:
   heating and cooling jackets within the chamber wall that facilitates adjusting the temperature of the chamber and solution.

10. The apparatus of claim 2, wherein the solution distributor further comprises:
    a sterilizer tank for eliminating biological organisms and contaminants and a manifold, wherein the sterilization tank is located in between and in liquid communication with the chamber and the manifold.

11. The apparatus of claim 2, which further comprises:
    filters for removing particulates from the solution before dispensing the solution into receptacles, wherein the filters are located in and in fluid communication with the solution distributor.

12. The apparatus of claim 1, wherein the reagents are solid reagents.

13. A solution preparation apparatus, the apparatus comprising:
    a plurality of containers for holding reagents;
    a dispensing mechanism in flow communication and operatively associated with each container that selectively and sequentially in a cumulative way dispenses an amount of one or more reagents;
    a balance, wherein the balance has a balance plate suitably dimensioned for receiving and suitably dimensioned for weighing in a cumulative way a plurality of sequentially dispensed reagents at the same time without loss of any reagent from the balance plate;
    a mixing chamber that receives the concentrated solution and additional liquids to adjust and prepare a liquid mixture of a predetermined concentration, wherein the mixing chamber has a chamber wall; and
    a supply that provides liquid to the balance for removing the reagents from the balance and forms a concentrated solution.

14. The apparatus of claim 1, further comprising probes associated with the mixing chamber for monitoring chemical and physical properties of the solution.

15. The apparatus of claim 1, which further comprises:
    a plurality of separate compartments, wherein each separate compartment houses a different section of the apparatus, and wherein the compartments can be scaled from the outside atmosphere by one or more airtight doors.

16. A solution preparation apparatus, the apparatus comprising:
    a plurality of containers for holding canisters;
    a plurality of conduits, wherein a single conduit is connected to and in flow communication with an egress end of one of the plurality of containers;
    one or more canisters containing solid reagents placed within a respective container, and connected to the egress end of the container so as to form an airtight seal between the canister and the conduit;
    a dispensing mechanism comprising:
      a plurality of valves connected to and in flow communication with the plurality of conduits; and
      a dispenser block supporting the valves and conduits, such that the dispensing mechanism is operatively associated with each container that selectively and sequentially dispenses an amount of one or more reagents;
    a balance comprising:
      one or more balance plate(s) that sequentially receives the dispensed reagent(s) from an egress end of each of the plurality of conduits, and weighs each received reagent;
    a supply that provides liquid to the balance for removing the reagents from the balance and forms a concentrated solution;

a chamber that receives the solution of solid reagents and liquid from the balance;

a volume setting system that determines the volume of solution within the chamber;

a pump that delivers liquid to the chamber until the volume setting system indicates the solution has reached a predetermined amount; and a valve that releases the solution from the solution into a manifold that dispenses the released solution into one or more receptacles.

17. A method of preparing solutions which comprises:

providing a plurality of reagents;

selectively and sequentially dispensing reagent(s) from reagent containers into a weighing zone, wherein the amounts of the one or more reagents dispensed into the weighing zone are each individually controlled by a computer actuated valve;

receiving the reagents selectively and sequentially in the weighing zone, wherein each dispensed reagent is separately weighed;

providing a liquid solvent;

spraying the liquid solvent into the weighing zone for rinsing the dispensed reagents from the weighing zone;

rinsing the one or more dispensed reagents from the weighing zone into a chamber with the spray of liquid solvent and forming a concentrated solution;

receiving the concentrated solution from the weighing zone in the chamber;

providing a liquid solvent to the chamber to dilute the concentrated solution;

diluting the concentrated solution from the weighing zone with additional liquid solvent to prepare a solution of predetermined concentration; and discharging the solution of predetermined concentration from the chamber to one or more solution receptacles.

18. The method of claim 17, further comprising:

providing one or more liquid reagents;

injecting one or more of the liquid reagents into the concentrated solution received in the chamber, wherein the liquid reagents adjust one or more properties of the concentrated solution; and recording the chemical and physical properties of the solution.

19. The method of claim 18, wherein the properties adjusted by injection of a liquid reagent includes pH.

20. A non-transitory computer-readable medium that stores computer-readable instructions for execution by a processing system, the computer readable instructions for preparing solutions comprising:

instructions to activate a valve for selectively and sequentially dispense reagent(s) from reagent containers into a weighing zone;

instructions to separately weigh each of the selectively and sequentially dispense reagent(s);

instructions to activate a pump for providing one or more liquid reagents for rinsing the one or more dispensed reagents from the weighing zone into a chamber;

instructions to activate a pump for providing a liquid solvent to the chamber to dilute the concentrated solution; and instructions to open a valve for discharging the solution of predetermined concentration from the chamber to one or more solution receptacles.

21. A solution preparation apparatus, the apparatus comprising:

a plurality of containers for holding reagents;

a dispensing mechanism in flow communication and operatively associated with each container that selectively and sequentially dispenses an amount of one or more reagents, wherein the reagents can be acids, bases, buffers or detergents or solutions of acids, bases, buffers or detergents or solid reagents;

a balance, wherein the balance has a balance plate suitably dimensioned for receiving and suitably dimensioned for weighing in a cumulative way a plurality of sequentially dispensed reagents at the same time without loss of any reagent from the balance plate;

a mixing chamber that receives the concentrated solution and additional liquids from the balance to adjust and prepare a liquid mixture of a predetermined concentration, wherein the mixing chamber has a chamber wall;

a probe associated with the mixing chamber for monitoring the chemical and physical properties of the solution;

a pump that delivers liquid to the chamber until the volume setting system indicates the solution has reached a predetermined amount;

a valve that releases the solution from the solution into a manifold that dispenses the released solution into one or more receptacles; and a plurality of filters for removing particulates from the solution before discharging the solution into one or more receptacles, wherein the filters are located in and in fluid communication with a solution distributor.

22. The apparatus of claim 21, wherein the solid reagent comprises a powder, crystal, pellet, grain, flake, filing, shaving or dust or any combination thereof.

23. The apparatus of claim 21, wherein the solid reagent comprises a pharmaceutical preparation.

24. The apparatus of claim 21, which further comprises:

heating and cooling jackets within the chamber wall that facilitates adjusting the temperature of the chamber and solution.

* * * * *